United States Patent
Feuerhake et al.

(10) Patent No.: US 8,283,496 B2
(45) Date of Patent: Oct. 9, 2012

(54) AMINOALKYL VINYL ETHERS COMPRISING ETHYLENIMINE UNITS, PROCESSES FOR THEIR PREPARATION AND THEIR USE

(75) Inventors: Robert Feuerhake, Mannheim (DE); Daniel Schoenfelder, Brussels (BE); Hans-Joachim Haehnle, Neustadt (DE); Bernd Bruchmann, Freinsheim (DE); Paola Uribe Arocha, Mannheim (DE); Alexander Kraus, Evenhausen (DE); Christian Huebsch, Gmund (DE); Bastiaan Bram Pieter Staal, Mannheim (DE); Ralph Baumgaertner, Mannheim (DE)

(73) Assignee: BASF SE, Ludwigshafen (DE)

( * ) Notice: Subject to any disclaimer, the term of this patent is extended or adjusted under 35 U.S.C. 154(b) by 264 days.

(21) Appl. No.: 12/680,210

(22) PCT Filed: Oct. 1, 2008

(86) PCT No.: PCT/EP2008/063111
§ 371 (c)(1), (2), (4) Date: Mar. 26, 2010

(87) PCT Pub. No.: WO2009/043860
PCT Pub. Date: Apr. 9, 2009

(65) Prior Publication Data
US 2010/0305362 A1 Dec. 2, 2010

(30) Foreign Application Priority Data
Oct. 4, 2007 (EP) ..................................... 07117909

(51) Int. Cl.
*C07C 217/04* (2006.01)
*C07C 213/02* (2006.01)
(52) U.S. Cl. ......... 564/505; 564/286; 564/294; 564/295
(58) Field of Classification Search .................... None
See application file for complete search history.

(56) References Cited

U.S. PATENT DOCUMENTS

| | | | |
|---|---|---|---|
| 2,727,019 A | 12/1955 | Melamed | |
| 2,969,395 A * | 1/1961 | Nedwick et al. | 564/391 |
| 3,314,927 A * | 4/1967 | Kelley | 526/288 |
| 6,562,926 B1 | 5/2003 | Decker et al. | |

FOREIGN PATENT DOCUMENTS

| | | |
|---|---|---|
| WO | 01 36500 | 5/2001 |
| WO | 2009 047148 | 4/2009 |

OTHER PUBLICATIONS

Database CAPLUS on STN, Acc. No. 1956:57158, Melamed, US 2727019 (Dec. 13, 1955) (abstract).*
Database CAPLUS on STN, Acc. No. 1963:20545, Nedwick, DE 1116214 (Nov. 2, 1961) (abstract).*
Database CAPLUS on STN, Acc. No. 1993:168696, EP 514710 A2 (Nov. 25, 1992) (abstract).*
Database CAPLUS on STN, Acc. No. 2008:226854, Russian Journal of Organic Chemistry (2007), 43(12), p. 1880-1881 (abstract).*
U.S. Appl. No. 12/741,244, filed May 4, 2010, Roller, et al.
U.S. Appl. No. 13/376,509, filed Dec. 6, 2011, Jehn-Rendu, et al.
U.S. Appl. No. 12/744,389, filed May 24, 2010, Feuerhake, et al.
Bektenov, et al., "New Anion Exchangers From a Copolymer of Glycidyl Methacrylate and Vinyl Ether of Monethanolamine", XP 002516263, Retrieved from STN Database accession No. 2001:548022. (Abstract only), (2001).

* cited by examiner

*Primary Examiner* — Brian J Davis
(74) *Attorney, Agent, or Firm* — Oblon, Spivak, McClelland, Maier & Neustadt, L.L.P.

(57) ABSTRACT

Aminoalkyl vinyl ethers comprising alkylenimine units and of the formula

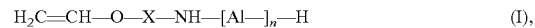

$$H_2C=CH-O-X-NH-[Al-]_n-H \qquad (I),$$

in which $[Al-]_n$ is a linear or branched oligoalkylenimine chain having n alkylenimine units, n is a number of at least 1 and X is a straight-chain or branched $C_2$- to $C_6$-alkylene group, and salts of the monomers I with mineral acids or organic acids and quaternization products of the monomers I with alkyl halides or dialkyl sulfates, processes for the preparation of the compounds of the formula I by addition reaction of alkylenimines with amino-$C_2$- to $C_6$-alkyl vinyl ethers and use of the aminoalkyl vinyl ethers comprising alkylenimine units and of the formula I as monomers for the preparation of polymers for use in the paper industry, as antimicrobial coating materials, in detergents and for the treatment of metal surfaces.

9 Claims, No Drawings

AMINOALKYL VINYL ETHERS COMPRISING ETHYLENIMINE UNITS, PROCESSES FOR THEIR PREPARATION AND THEIR USE

The invention relates to aminoalkyl vinyl ethers comprising ethylenimine units and of the formula $$H_2C=CH-O-X-NH-[Al-]_n-H \quad (I).$$

in which
[Al—]$_n$ is a linear or branched oligoalkylenimine chain having n alkylenimine units,
n is a number of at least 1 and
X is a straight-chain or branched $C_2$- to $C_6$-alkylene group,
and salts and quaternization products of the monomers I, processes for their preparation and their use as monomers for the preparation of polymers for use in the paper industry, as antimicrobial coating materials, in detergents and for the treatment of metal surfaces.

WO-A-01/36500 discloses monomers comprising alkylenimine units and of the formula

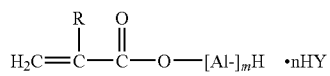

in which
R is hydrogen or $C_1$- to $C_4$-alkyl,
[Al—]$_m$ is a linear or branched oligoalkylenimine chain having m alkylenimine units,
m is an integer in the range from 1 to 20, and the number average m in the oligoalkylenimine chains is at least 1.5,
Y is the anion equivalent of a mineral acid and
n is a number $1 \leq n \leq m$.

Monomers or monomer mixtures in which, in the above-mentioned formula, the number average of m is at least 2.1, in general from 2.1 to 8, are preferred. They are obtainable by reacting an ethylenically unsaturated carboxylic acid with an oligoalkylenimine, preferably in the form of an oligomer mixture. The resulting product can, if appropriate, be converted into the acid addition salt with a mineral acid HY. Such monomers can be polymerized in an aqueous medium in the presence of an initiator which initiates a free radical polymerization to give homo- and copolymers which are used as assistants in papermaking.

The object of the invention is to provide further monomers having alkylenimine units.

The object is achieved, according to the invention, by aminoalkyl vinyl ethers comprising alkylenimine units and of the formula $$H_2C=CH-O-X-NH-[Al-]_n-H \quad (I),$$

in which
[Al—]$_n$ is a linear or branched oligoalkylenimine chain having n alkylenimine units,
n is a number of at least 1 and
X is a straight-chain or branched $C_2$- to $C_6$-alkylene group,
and salts of the monomers I with mineral acids or organic acids and quaternization products of the monomers I with alkyl halides or dialkyl sulfates.

Linear oligoalkylenimine chains [Al—]$_n$ can be described, for example, with the aid of the following formula $$-[CHR'-CHR''-NH-]_n-H \quad (II),$$

in which n is a number of at least 1 and R' and R'' are monovalent organic radicals, such as $C_1$- to $C_4$-alkyl, phenyl or hydrogen. R' and R'' are preferably hydrogen.

Branched oligoalkylenimine structures [Al—]$_n$ can be characterized, for example, with the aid of the following formula

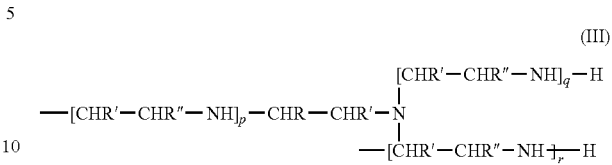

in which p is 0 or an integer 1, 2, 3, etc differing from 0, q and r, independently of one another are, integers differing from 0 and the sum p+q+r+1 is n. The formula III represents a singly branched oligoalkylenimine unit [Al—]$_n$, but multiple branches are also possible.

Aminoalkyl vinyl ethers comprising alkylenimine units and of the formula I in which
[Al—]$_n$ is n ethylenimine units,
n is a number from 2 to 20 and
X is a $C_3$- to $C_4$-alkylene group
are preferred.

Aminoalkyl vinyl ethers comprising alkylenimine units and of the formula I in which
[Al—]$_n$ is n ethylenimine units,
n is a number from 3 to 15 and
X is the group —$CH_2$—$CH_2$—$CH_2$—
are particularly preferred.

In the case of the salts of the monomers I with mineral acids or with organic acids, at least one of the nitrogen atoms present therein, preferably a plurality or all (i.e. n+1 in formula I) of nitrogen atoms present therein, is or are present in protonated form. They can therefore be partly or completely neutralized. For example, mineral acids, such as hydrochloric acid, sulfuric acid, phosphoric acid, phosphonic acid or nitric acid, or organic acids, such as formic acid, acetic acid, propionic acid, benzenesulfonic acid, amidosulfonic acid or p-toluenesulfonic acid, are suitable for salt formation.

The quaternization products of the monomers I are obtainable by reaction of the monomers I with quaternizing agents, such as $C_1$- to $C_{18}$-alkyl halides or dialkyl sulfates. At least one nitrogen atom of the nitrogen atoms present in the monomers I is present in quaternized form in the quaternization products. Quaternized monomers I comprise, for example, from 2 to not more than n+1 quaternized nitrogen atoms, n having the meaning stated above in the formula I. Suitable quaternizing agents are, for example, methyl chloride, ethyl chloride, n-propyl chloride, isopropyl chloride, n-butyl chloride, sec-butyl chloride, n-hexyl chloride, cyclohexyl chloride, benzyl chloride, methyl bromide, methyl iodide, ethyl bromide, ethyl iodide, dimethyl sulfate and diethyl sulfate.

Aminoalkyl vinyl ethers comprising alkylenimine units and of the formula I are obtainable by subjecting at least one alkylenimine to an addition reaction with amino-$C_2$- to $C_6$-alkyl vinyl ethers, at least 1 mol of an alkylenimine being used per mole of the vinyl ether, and neutralizing the adducts with a mineral acid or an organic acid for the preparation of the salts and reacting them with $C_1$- to $C_{18}$-alkyl halides or dialkyl sulfates for the preparation of the quaternization products.

In a preferred embodiment of the process according to the invention, ethylenimine is subjected to an addition reaction with amino-$C_3$- to $C_4$-alkyl vinyl ethers, from 2 to 20 mol of ethylenimine being subjected to the addition reaction per mole of the vinyl ether.

The reaction products of aminopropyl vinyl ether with ethylenimine in the molar ratio of from 1:3 to 15 are particularly preferred. In the $^1$H-NMR spectrum, they show a multiplet at from 2.54 to 2.78 ppm, that of the signals of the protons which are adjacent to the amino group in the aminoalkyl vinyl ether (—CH$_2$—NH$_2$) and the signals of the protons of this group in the form oligomerized with ethylenimine. The aminopropyl vinyl ether oligomerized with ethylenimine has a cationic charge density of 9.0 meq/g (measured in an aqueous solution at a pH of 8, a concentration of 0.1 g/kg and a temperature of 20° C.) at a degree of oligomerization of n=6.8.

The reaction of alkyl vinyl ethers with alkylenimines is preferably carried out in an aqueous medium in the presence of a catalyst, for example a mineral acid. Sulfuric acid is preferably used as a catalyst. For example, one mole of a catalyst, such as sulfuric acid, is first allowed to react with from 60 to 85 mol, preferably from 70 to 75 mol, of an aminoalkyl vinyl ether and ethylenimine is then subjected to an addition reaction with the aminoalkyl vinyl ether, which is present partly as an ammonium salt. The pH of the reaction mixture is, for example, in the range of ≧6.5, preferably from 8 to 11. The reaction temperature is, for example, from 55 to 105° C. It is generally in the temperature range from 60 to 80° C., in particular from 65 to 75° C.

The addition reaction of the alkylenimines, preferably of ethylenimine, with aminoalkyl vinyl ethers is carried out, for example, in a manner such that at least one aminoalkyl vinyl ether is dissolved in water at room temperature, a catalyst, such as sulfuric acid, is added to the aqueous solution, the mixture is heated to the reaction temperature with stirring and the alkylenimine is metered continuously or in portions with continuous stirring into the initially taken mixture so that the alkylenimine reacts in a controlled manner and the reaction temperature can be regulated. The reaction time required for this purpose is, for example, from 10 minutes to 3 hours on the laboratory scale, depending on the size of the batch. The end point of the reaction, i.e. the time when alkylenimine can no longer be detected in the reaction mixture, is determined with the aid of the reaction of ethylenimine with 4-(4-nitrobenzyl) pyridine, cf. R. Preussmann, H. Schneider and F. Epple, Arzneimittel-Forschung, volume 19, 1059-1073 (1969). In said test, with 4-(4-nitrobenzyl)pyridine, ethylenimine is detected on the basis of an intense violet color. If this test is negative, the reaction is complete. The reaction mixture can be used directly. However, it is also possible to isolate the adduct of ethylenimine with the aminoalkyl vinyl ether from the reaction mixture, for example by removal of water.

The aminoalkyl vinyl ethers according to the invention comprising alkylenimine units are monomers which can be polymerized with the aid of free radical initiators. They are therefore used as monomers for the preparation of polymers for use in the paper industry. Polymers having molar masses M$_w$ of up to 30 000 are suitable, for example, as fixing agents for pitch and crill in papermaking. Polymers of the monomers of the formula I can also be used as antimicrobial coating materials, in detergents and for the treatment of metal surfaces.

EXAMPLE 1

30 g (0.296 mol) of aminopropyl vinyl ether (CH$_2$=CH—O—CH$_2$—CH$_2$—CH$_2$—NH$_2$) are dissolved in 16 g of demineralized water and mixed with 5 g of concentrated sulfuric acid (0.051 mol) in a four-necked flask which was equipped with a stirrer, a thermometer and metering apparatus. The pH was 8.5. The mixture was heated to a temperature of 65° C. in a nitrogen atmosphere with stirring. As soon as this temperature was reached, 161 ml of a 60% strength aqueous solution of ethylenimine (89.4 g, 2.079 mol) were metered in the course of one hour. The mixture was then stirred for a further four hours at a temperature in the range from 65 to 70° C. After this time, ethylenimine could no longer be detected in the reaction mixture with the aid of the abovementioned Preussmann test. After the end of the reaction, the pH of the reaction mixture was 11.

EXAMPLE 2

78.2 g (0.772 mol) of aminopropyl vinyl ether (CH$_2$=CH—O—CH$_2$—CH$_2$—CH$_2$—NH$_2$) are dissolved in 41.7 g of demineralized water and slowly adjusted to a pH of 11 with 10% concentrated sulfuric acid in a four-necked flask with intensive stirrer, reflux condenser and thermometer. The mixture was heated to a temperature of 65° C. in a nitrogen atmosphere with stirring. As soon as this temperature had been reached, 360 ml of a 60% strength aqueous solution of ethylenimine (199.7 g, 4.644 mol) were metered in in the course of one hour. The mixture was then kept at 65° C. for a further hour and then stirred for a further four hours at 85° C. Finally, the mixture was refluxed for a further three hours. After this time, ethylenimine could no longer be detected in the reaction mixture with the aid of the abovementioned Preussmann test.

EXAMPLE 3

180 g (1.776 mol) of aminopropyl vinyl ether (CH$_2$=CH—O—CH$_2$—CH$_2$—CH$_2$—NH$_2$) were dissolved in 25 g of demineralized water and slowly adjusted to a pH of 11 with 10% concentrated sulfuric acid in a four-necked flask with intensive stirrer, reflux condenser and thermometer. The mixture was heated to a temperature of 65° C. in a nitrogen atmosphere with stirring. As soon as this temperature had been reached, 276 ml of a 60% strength aqueous solution of ethylenimine (153.3 g, 3.565 mol) were metered in in the course of one hour. The mixture was then stirred for 30 minutes at 70° C. Finally, the mixture was refluxed for a further five hours. After this time, ethylenimine could no longer be detected in the reaction mixture with the aid of the abovementioned Preussmann test.

The invention claimed is:

1. An aminoalkyl vinyl ether comprising alkylenimine units, said vinyl ether having the formula

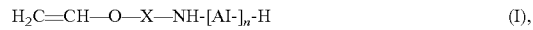

$$H_2C=CH-O-X-NH-[AI-]_n-H \qquad (I),$$

in which
    [AI-]$_n$ is a branched oligoalkylenimine chain having n alkylenimine units,
    n is a number of at least 1 and
    X is a straight-chain or branched C$_2$- to C$_6$-alkylene group,
    and salts of the monomers I with mineral acids or organic acids and quaternization products of the monomers I with alkyl halides or dialkyl sulfates.

2. The aminoalkyl vinyl ether comprising alkylenimine units according to claim 1, wherein, in the formula I,
    [AI-]$_n$ is n ethylenimine units,
    n is a number from 2 to 20 and
    X is a C$_3$- to C$_4$-alkylene group.

3. The aminoalkyl vinyl ether comprising alkylenimine units according to claim 1, wherein, in the formula I,
    [AI-]$_n$ is n ethylenimine units
    n is a number from 3 to 15 and
    X is the group —CH$_2$—CH$_2$—CH$_2$—.

4. A process for the preparation of an aminoalkyl vinyl ether comprising alkylenimine units, said vinyl ether having the formula $$H_2C=CH-O-X-NH-[AI-]_n-H \quad (I),$$

in which
[AI-]$_n$ is a linear or branched oligoalkylenimine chain having n alkylenimine units,
n is a number of at least 1 and
X is a straight-chain or branched $C_2$- to $C_6$-alkylene group,
or a salt of the monomers I with a mineral acids or an organic acid,
or a quaternization product of the monomers I with an alkyl halide or a dialkyl sulfate, wherein at least one alkylenimine is subjected to an addition reaction with an amino-$C_2$- to $C_6$-alkyl vinyl ether, at least 1 mol of an alkylenimine being used per mole of the vinyl ether, and the adduct is neutralized with a mineral acid or an organic acid for the preparation of the salt and they are reacted with a $C_1$- to $C_{18}$-alkyl halide or dialkyl sulfate for the preparation of the quaternization product.

5. The process according to claim 4, wherein ethylenimine is subjected to an addition reaction with an amino-$C_3$- to $C_4$-alkyl vinyl ether, from 2 to 20 mol of ethylenimine being subjected to the addition reaction per mole of the vinyl ether.

6. The process according to claim 4, wherein the aminopropyl vinyl ether is reacted with ethylenimine in the molar ratio of from 1:3 to 15.

7. A polymer obtained by polymerizing the aminoalkyl vinyl ether according to claim 1.

8. The aminoalkyl vinyl ether comprising alkylenimine units according to claim 1, wherein, in the formula I, [AI-]$_n$, has the following formula III:

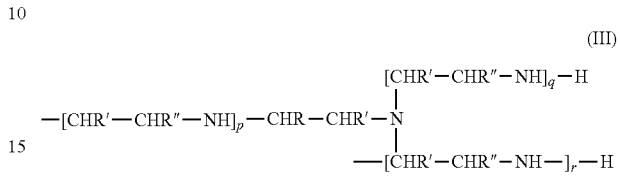

(III)

wherein p is 0 or an integer, q and r, independently of one another are, integers other than 0 and n is the sum p+q+r+1.

9. The aminoalkyl vinyl ether comprising alkylenimine units according to claim 8, wherein formula III represents a singly branched oligoalkylenimine unit [AI-]$_n$, and [AI-]$_n$ consists of multiple branches of said formula III.

* * * * *